(12) United States Patent
Liu et al.

(10) Patent No.: US 10,744,211 B2
(45) Date of Patent: Aug. 18, 2020

(54) TRIFUNCTIONAL AND COMPLETELY CLEARABLE SPECIFIC TARGETING AGENTS AND METHODS THEREOF

(71) Applicant: University of Massachusetts, Boston, MA (US)

(72) Inventors: Guozheng Liu, Worcester, MA (US); Shuping Dou, Worcester, MA (US)

(73) Assignee: University of Massachusetts, Boston, MA (US)

( * ) Notice: Subject to any disclaimer, the term of this patent is extended or adjusted under 35 U.S.C. 154(b) by 61 days.

(21) Appl. No.: 15/939,230

(22) Filed: Mar. 28, 2018

(65) Prior Publication Data
US 2018/0250425 A1    Sep. 6, 2018

Related U.S. Application Data

(63) Continuation of application No. 14/250,632, filed on Apr. 11, 2014, now abandoned.

(60) Provisional application No. 61/811,676, filed on Apr. 12, 2013.

(51) Int. Cl.
| | |
|---|---|
| *A61K 51/10* | (2006.01) |
| *A61K 49/00* | (2006.01) |
| *A61K 51/06* | (2006.01) |
| *A61K 51/04* | (2006.01) |
| *A61K 47/68* | (2017.01) |

(52) U.S. Cl.
CPC .......... *A61K 49/00* (2013.01); *A61K 47/6898* (2017.08); *A61K 51/0495* (2013.01); *A61K 51/065* (2013.01)

(58) Field of Classification Search
CPC .... A61K 49/00; A61K 47/00; A61K 47/6898; A61K 51/00; A61K 51/0495; A61K 51/065; A61K 51/10
USPC .......... 424/1.11, 1.49, 1.65, 1.81, 1.85, 1.89, 424/9.1, 9.2, 9.3, 9.4, 9.5, 9.6; 206/227, 206/569, 570; 534/7, 10–16; 530/300; 514/1, 1.1
See application file for complete search history.

(56) References Cited

U.S. PATENT DOCUMENTS 6,899,864 B2 * 5/2005 Hnatowich ........ A61K 51/0495
424/1.65

FOREIGN PATENT DOCUMENTS

WO    WO-2004091525 A2 * 10/2004 ........... A61K 51/065

* cited by examiner

*Primary Examiner* — D. L. Jones
(74) *Attorney, Agent, or Firm* — Milstein Zhang & Wu LLC

(57) ABSTRACT

The invention provides a novel trifunctional targeting construct and related compositions and methods that are useful in therapeutic, diagnostic (including imaging) of various biological and/or pathological conditions and diseases such as cancers and diabetes. The trifunctional targeting construct of the invention provides enhanced clearing step and reduced non-specific background via complete clearance of undesired antibody conjugates.

3 Claims, 13 Drawing Sheets

TRIFUNCTIONAL AND COMPLETELY CLEARABLE SPECIFIC TARGETING AGENTS AND METHODS THEREOF

PRIORITY CLAIMS AND RELATED APPLICATIONS

This application claims the benefit of U.S. Provisional Application No. 61/811,676, filed Apr. 12, 2013, the entire content of which is incorporated herein by reference in its entirety.

GOVERNMENT RIGHTS

This invention was made with Government support under Grant No. DK094199 awarded by the National Institutes of Health. The Government has certain rights in the invention.

TECHNICAL FIELD OF THE INVENTION

The invention generally relates to therapeutics and diagnostics of biological and/or pathological conditions. More particularly, the invention relates to a unique trifunctional targeting construct for targeted delivery of therapeutic or diagnostic agents, and related compositions and methods of use and preparation. The compositions and methods of the invention are useful in treatment and/or diagnosis (including imaging) of various conditions and diseases such as cancers and pancreatic islets in connection with diabetes.

BACKGROUND OF THE INVENTION

Targeted drug delivery is of critical importance in ensuring safety and efficacy of therapeutic and diagnostic agents. In cancer treatment and diagnosis, for example, targeted delivery directly to the tumor site allows more effective dosing at the tumor sites than systemic delivery, therefore increasing drug effectiveness while reducing side effects. Diagnostic or therapeutic agents conjugated to targeting moieties such as antibodies or antibody fragments, cell- or tissue-specific peptides, hormones and other receptor binding molecules have previously been studied. (See, e.g., U.S. Pat. Nos. 3,927,193, 4,331,647, 4,348,376, 4,361,544, 4,468,457, 4,444,744, 4,460,459, 4,460,561, 4,624,846 and 4,818,709).

A significant challenge for direct targeting methods, such as through antibody vectors, is that a relatively small fraction of the conjugate actually binds to the target site, while the majority of the antibody conjugate molecules remain in circulation. Such antibody-agent conjugate molecules often negatively affect the functionality of the active agent and cause undesirable marrow toxicity or other systemic side effects. Besides limiting dosing, the circulating antibody-agent conjugate molecules also increase background noise and reduce resolution in a diagnostic application. In islet imaging, because islets constitute only 1-2% of the pancreatic mass, additional difficulty appears within the organ and highly specific delivery is more crucial. (See, e.g., Liu, et al. 2011 *Mol. Pharmaceutics* 8, 767-773; Liu, et al. 2012 *Nuclear Medicine and Biology* 39, 645-651.)

To increase the target to background ratios, pretargeting methods and clearing agents have been studied. An example of pretargeting method is a (strept)avidin-biotin system. Another example is the use of the bispecific antibody-hapten recognition system, which uses a radiolabeled hapten and a bispecific antibody in place of (strept)avidin and biotin. (See, e.g., Barbet, et al. 1999 *Cancer Biother. Radiopharm.* 14:153-166; Karacay, et al. 2000 *Bioconj. Chem.* 11: 842-854; Gautherot, et al. 2000 *J. Nucl. Med.* 41:480-487; Lubic, et al. 2001 *J. Nucl. Med.* 42:670-678; Gestin, et al. 2001 *J. Nucl. Med.* 42:146-153.) However, the affinity of an antibody for its hapten, particularly for a monovalent one, is orders of magnitude lower than that of (strept)avidin for biotin.

Existing targeting and clearance systems, however, suffer from low clearance efficiency as well as nonspecific background, which remain as major hurdles to creating an effective targeted delivery system. A novel pretargeting approach is especially desired that has enhanced clearing effectiveness and reduced non-specific background.

SUMMARY OF THE INVENTION

The invention provides a unique trifunctional targeting construct and related compositions and methods that are useful in therapeutics and diagnosis (including imaging) of various biological and/or pathological conditions and diseases. The trifunctional targeting construct of the invention enables a much enhanced clearing mechanism and significantly reduced non-specific background via the completely clearable antibody construct.

In one aspect, the invention generally relates to a conjugate compound. The compound includes: a targeting moiety capable of selectively binding to a primary and specific target site or to a substance produced by or associated with the target site; a first conjugate moiety comprising two covalently linked ligand groups, a first ligand group and a second ligand group; and a covalent linkage between the targeting moiety and the first conjugate to form a second-order conjugate compound.

In another aspect, the invention generally relates to a kit for delivering a diagnostic or therapeutic agent to a target site. The kit includes: (a) a compound that include: a targeting moiety capable of selectively binding to a primary and specific target site or to a substance produced by or associated with the target site, a first conjugate comprising two covalently linked ligand groups, a first ligand group and a second ligand group, and a covalent linkage between the targeting moiety and the first conjugate; (b) a clearing agent comprising a group capable of selective binding to the second ligand group; and (c) an effector conjugate, wherein the effector conjugate comprises an effecting group covalently linked to a group capable of selective binding to the first ligand group.

In yet another aspect, the invention generally relates to a method for targeted delivery of an agent to a target site in a mammal. The method includes: (a) administering to the mammal a first compound. The first compound includes: a targeting moiety capable of selectively binding to a primary and specific target site or to a substance produced by or associated with the target site, a first conjugate comprising two covalently linked ligand groups, a first ligand group and a second ligand group, and a second conjugate formed by a covalently linkage between the targeting moiety and the first conjugate; (b) administering to the mammal a clearing agent comprising a group capable of selective binding to the second ligand; and (c) administering to the mammal an effector conjugate, wherein the effector conjugate comprises an agent covalently linked to a group capable of selective binding to the first ligand group.

DETAILED DESCRIPTION OF THE INVENTION

Figure 1:
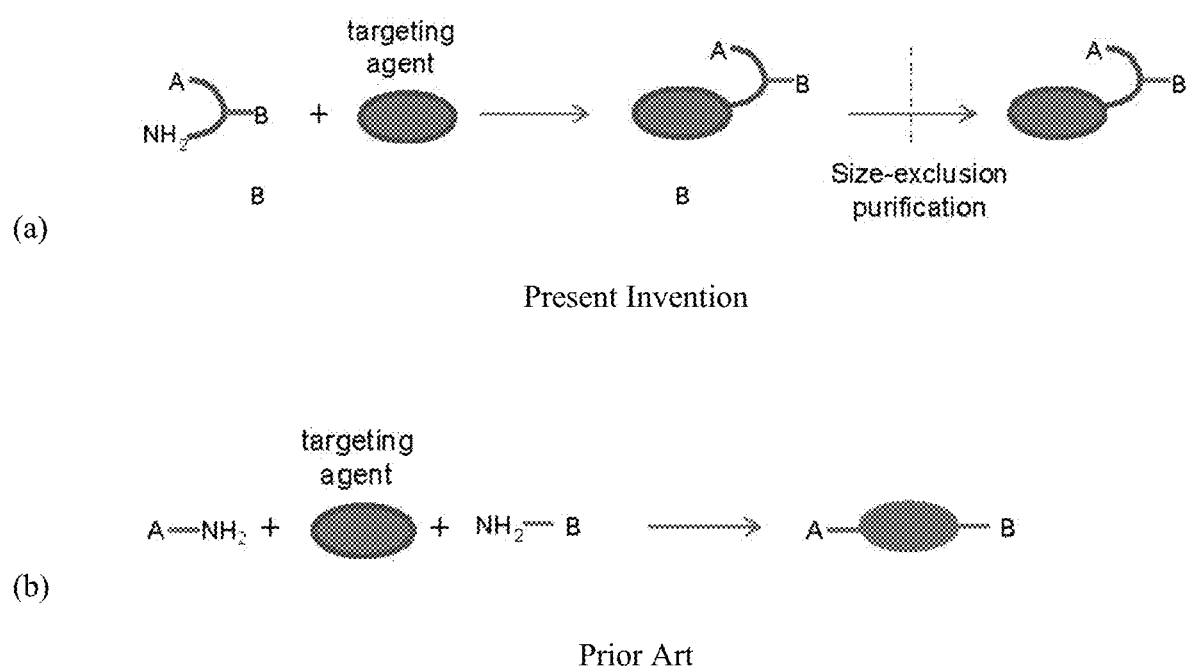
FIG. 1 schematically illustrates the different approaches between the present invention (a) and the prior art (b).

The present invention provides a unique targeting construct, and related compositions and methods of use and preparation, which are useful in treatment and diagnosis (including imaging) of various biological and/or pathological conditions and diseases such as cancers and diabetes. The trifunctional targeting construct of the invention ensures minimization of the undesirable by-products while significantly reduces non-specific background via complete clearance of undesired antibody conjugates.

Monoclonal antibodies have been investigated as targeted therapeutic and imaging agents for many years. The recent exciting success in hematological cancer therapy highlights the importance of the "magic bullet" concept. However, compared to the hematological cancers, solid tumor therapy would be more challenging because of its lower accessibility. Increasing the toxicity or the dose of the "warhead" would address the required toxic effect for tumor therapy, but the toxicity to normal tissues would be elevated at the same time. A solution is to clear the circulating antibody out of normal organs after the tumor accumulation essentially completes. In addition for therapy, the clearance concept may also be important for tumor imaging as well in certain circumstances, for example, using antibody to image the islet of Langerhans. (Liu, et al. 2012 Nucl. Med. Biol. 39, 645-651; Liu, et al. 2011 Mol. Pharmaceutics 8, 767-773.) Because islets constitute only 1-2% of the pancreas mass and the current nuclear imaging technologies cannot differentiate islets from non-islet pancreatic tissues, reduction of the non-specific binding in the exocrine tissues is critical.

Currently, there are two clearing mechanisms in the literature. The secondary antibody mechanism takes advantage of the big size of the aggregate formed between the secondary antibody and the pretargeting antibody to remove the latter from the circulation by the reticuloendothelial (RE) cells. (Goodwin, et al. 1988 J. Nucl. Med. 29, 226-234; Goodwin, et al. 1994 Cancer Res. 54, 5937-5946.) The saccharide mechanism employs the clearing agents bearing saccharide groups, for example, avidin, galactosylated antiantibodies against the pretargeting antibody, and galactosylated and biotinylated HSA. The complexes formed between antibody and clearing agent are removed by an asialoglycoprotein receptor. Both mechanisms traffic the circulating pretargeting molecules into liver. However, although the concept was considered extensively for its application in tumor pretargeting, few efforts were invested to understand the in vivo interaction between the antibody and the clearing agent. (Yao, et al. 1995 J. Nucl. Med. 36, 837-841; Wang, et al. 2001 Bioconjug. Chem. 12, 807-816; Karacay, et al. 1997 Bioconjug. Chem. 8, 585-594; Sharkey, et al. 1997 Bioconjug. Chem. 8, 595-604; Axworthy, et al. 2000 Proc. Natl. Acad. Sci. U.S.A. 97, 1802-1807; Mirallie, et al. 2005 Eur. J. Nucl. Med. Mol. Imaging. 32, 901-909; Liu, et al. 2010 Cancer Biother. Radiopharm. 25, 757-762; Ashwell, et al. 1974 Adv. Enzymol. 41, 99-128; Ong, et al. 1991 Cancer Res. 51, 1619-1626; Kobayashi, et al. 1995 Eur. J. Cancer 31, 1689-1696.)

The current investigation employs a model pretargeting system to exemplify an investigation into the in vivo chemistry between a clearing agent and a biotinylated IgG antibody. In this system, the antibody CC49 as the pretargeting agent is conjugated concomitantly with a morpholino phosphorodiamidate oligomer (MORF) for its radiolabeling in vivo and in vitro and with a biotin for binding to the clearing agent of avidin. The radiolabeling of the biotin-antibody-MORF was achieved by binding to the radiolabeled MORF complement (cMORF). In contrast to most clearance systems reported in the literature, the avidin binding of the antibody in this design does not compete or interfere with its effector binding.

The trifunctional antibody conjugate of the invention includes a functionality for effective and complete blood clearance and another functionality for binding to a later administrated effector (e.g., a therapeutic effector or a biomarker probe) that are together linked to the targeting moiety (e.g., an antibody). For example in tumor targeting, as schematically illustrated in FIG. 1(a), a clearance group ("A") plus an amine modified effector-binding agent ("B") is attached to a tumor-specific targeting agent ("C"), such that when the amine becomes linked to the tumor targeting agent, each A on the tumor targeting agent is with a function B.

Unlike the previous constructs, illustrated in FIG. 1(b), where A and B are reacted simultaneously with a targeting agent to form the conjugate, the present invention is designed to ensure that each B is covalently linked to an A and vice versa before they concomitantly are conjugated on to the targeting agent. Thus, there is no possibility that only A or only B is conjugated to the targeting agent. Even if there is impurity that is not modified with amine, each B on the targeting agent is still with a function A, because the unmodified A-B does not react with the targeting agent. Size-exclusion purification can easily remove the unmodified A-B.

Figure 2:
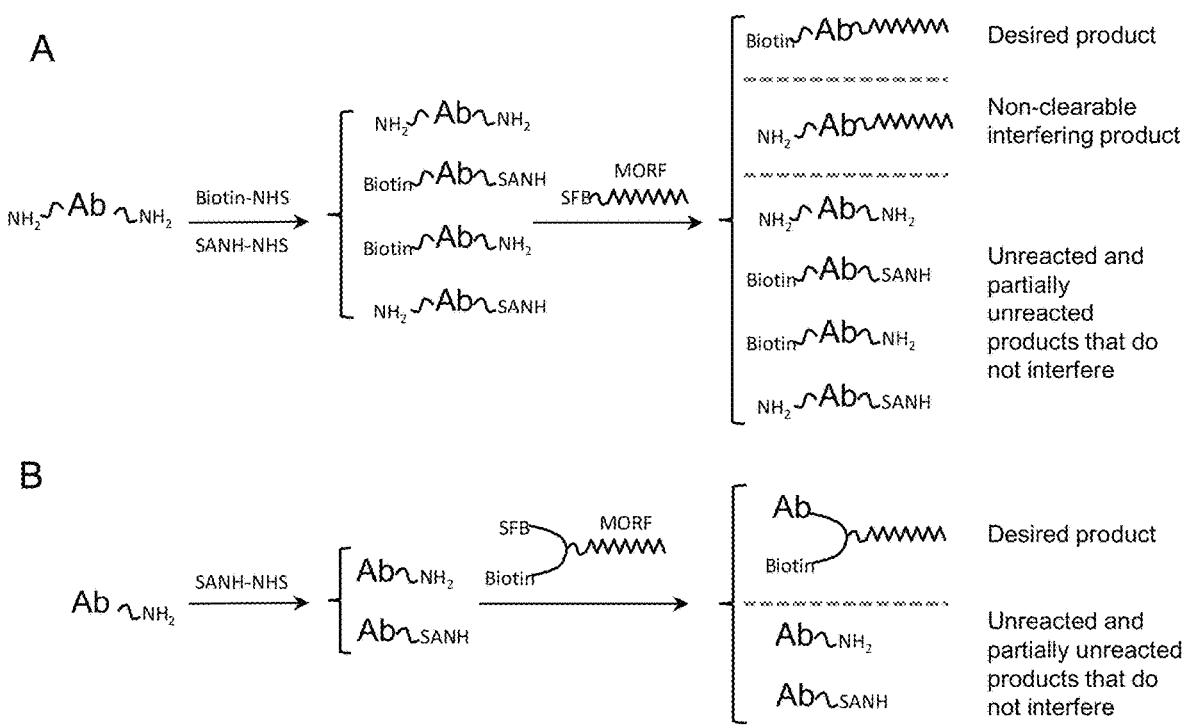
FIG. 2 schematically illustrates an exemplary chemical modification (A) of an antibody by both a biotin and a MORF that may produce a mixture of desired clearable product, undesired non-clearable product, and non-interfering unmodified and partially unmodified antibody molecules; and a new design (B) to modify the antibody by SFB-derivatized (biotin-MORF) that produces only the desired clearable antibody together with the non-interfering unmodified and partially unmodified antibody molecules. SANH and SFB are the paired agents in the commercial Hydralink approach to link two groups together. MORF is a DNA analogue of morpholino oligomer that binds to its complement, cMORF (the pretargeting effector).

While not wishing to be bound by the theory presented herein, an explanation for the persistent low clearance of existing targeting and preclearance strategies is the formation of a product mixture, for example, in a statistical distribution. FIG. 2A schematically illustrates the chemical modification of an antibody by both a biotin and a MORF that may produce a mixture of desired clearable product, undesired non-clearable product, and non-interfering unmodified and partially unmodified antibody molecules. The product mixture from modifying an antibody with both NHS-biotin (clearance function) and NHS-SANH plus SFB-MORF (effector-binding function) in the previous art could produce three different types of products: the desired product with both biotin and MORF, the undesired by-product with only MORF, and the unreacted and partially unreacted antibody molecules without MORF. (Liu, et al. 2010 *Cancer Biother Radiopharm* 25:757-62.) Size-exclusion purification would not remove the by-product such that the MORF-antibody injectate would not be completely clearable.

An exemplary embodiment of a synthetic route according to the invention is schematically illustrated in FIG. 2B. Biotin and MORF groups are conjugated together to an antibody such that each MORF (an effector-binding group) was together with a biotin. This unique tri-functional (avidin-MORF)-antibody pretargeting construct enables complete clearance of circulating antibody conjugates. Here, the synthetic approach employs a mechanism that assures that each MORF on the antibody co-exists with a biotin.

For example, a 3'-($NH_2$-biotin)-MORF was designed, custom-synthesized, and characterized. After confirming each amine was bound to a biotin by radiolabeling with $^{99m}$Tc at the amine position and measuring the percent bound to streptavidin, the ($NH_2$-biotin)-MORF was conjugated to a model IgG antibody using a commercial Hydralink method. The MORF impurity without ($NH_2$-biotin) modification essentially could not be attached to the antibody and therefore could be removed during purification by size exclusion. The (biotin-MORF)-antibody was labeled via MORF/cMORF-$^{99m}$Tc hybridization and evaluated in mice for the clearance efficiency by avidin. For a ($NH_2$-biotin) sample, 75% of the MORF was found with the ($NH_2$-biotin) modification; however, every amine was with a biotin. The MORF was readily conjugated to the model antibody at an average of 1.17 (MORF-biotin)s per antibody. Biodistributions of the radiolabeled (biotin-MORF)-antibody with and without avidin indicated that the antibody was almost completely clearable (96% from blood at 2 and 4 h) and, as expected, the radioactivity was cleared to liver. Thus, by conjugating an amine-plus-biotin modified MORF to an antibody, a completely clearable antibody construct can be made available for future pretargeting applications.

Thus, provided herein is a validated construct for modifying an antibody with two functions (e.g., MORF and biotin) as a pretargeting agent that is completely clearable from circulation. Even though the MORF was not pure, each MORF on the antibody in the product was with a biotin because only the ($NH_2$-biotin)-modified MORF would react with the antibody. The pretargeting construct obtained in this fashion is tri-functional, i.e., capable of binding to tumor, clearing agent, and radiolabeled effector. The previous double modification also provided a tri-functional product, but may contain non-clearable impurity because conjugation of two separate groups onto an antibody led to a statistical distribution. (Mirallie, et al. 2005 *Eur J Nucl Med Mol Imaging* 32:901-9; Liu, et al. 2010 *Cancer Biother Radiopharm* 25:757-62.)

Two methods have been employed to measure the number of biotins on the MORF as measures of quality insurance for the above mentioned 3'-($NH_2$-biotin)-MORF sample. Both indicated that the modification was incomplete, although the values from the two methods were not identical (0.64 vs 0.75±0.01). Systematic errors from different methods may reasonably account for the difference. First, quantitation of the MORF by spectrophotometry for the 0.64 biotin per MORF was after hydrolyzing the MORF by 0.1 N HCl and calculated from the molar absorbance provided by providers, while the HPLC detector was measuring intact MORF. As HPLC measures peak area relative to the internal standard, the 0.75±0.01 may be more accurate. In addition, both methods assumed the MORF sequence was pure, but the realty would never be so. The peak shape of the MORF that did not bind to avidin was not identical to that of the total MORF (more easily appreciated if the MORF peaks in FIG. 4B were adjusted to the same height). Assuming the height was also proportional to the amount as should be in principle, the data led to a larger value of 0.84±0.00 biotins per MORF.

In an experiment testing clearablity, avidin and biotinylated antibody were combined before administering them to animals. It was evident that, if bound to an avidin, a biotinylated antibody clear rapidly and completely. This result therefore excludes any possibility that the low clearance efficiency in the old art was due to a fraction of the avidin-bound antibody still in the circulation. (Liu, et al. 2010 *Cancer Biother Radiopharm* 25:757-62; Liu, et al. 2010 *Q J Nucl Med Mol Imaging* 54:333-40.). Though not directly relating to the theory in this invention, the rapid clearance may reduce the risk of immunogenicity of avidin, a concern naturally arising from the fact that streptavidin was immunogenic especially when attached to antibody. (Knox, et al. 2000 *Clin Cancer Res.* 6: 406-14.). Indeed, no immunogenicity for avidin was ever been reported after IV injection probably due to its rapid clearance. (Sinitsyn, et al. 1989 *J Nucl Med* 30: 66-9.) Subcutaneous injection did induce immunogenicity, but the period of presence was prolonged. (Caliceti, et al. 2002 *J Controlled Release* 83: 97-108.). Thus, immunogenicity for avidin is unlikely to occur if IV injection is used due to rapid clearance.

Thus, in one aspect, the invention generally relates to a conjugate compound. The compound includes: a targeting moiety capable of selectively binding to a primary and specific target site or to a substance produced by or associated with the target site; a first conjugate moiety comprising two covalently linked ligand groups, a first ligand group and a second ligand group; and a covalent linkage between the targeting moiety and the first conjugate to form a second-order conjugate compound.

The targeting moiety may be any suitable group dependent on the application. In certain embodiments, the targeting moiety is an antibody or an antibody fragment. Preferred are the monoclonal antibodies (Mabs) due to their high specificities. Mabs may be prepared by procedures of immunization of mammals with immunogenic antigen preparation, fusion of immune lymph or spleen cells with an immortal myeloma cell line, and isolation of specific hybridoma clones. Other methods of preparing monoclonal antibodies are also contemplated, such as interspecies fusions and genetic engineering manipulations of hypervariable regions, since it is primarily the antigen specificity of the antibodies that affects their utility in the present invention. It will be appreciated that newer techniques for production of monoclonals can also be used, e.g., human monoclonals, interspecies monoclonals, chimeric (e.g., human/mouse) monoclonals, genetically engineered antibodies and the like.

Useful antibody fragments include, for example, F(ab')$_2$, F(ab)$_2$, Fab', Fab, Fv and the like including hybrid fragments. Preferred fragments are Fab', F(ab')$_2$, Fab, and F(ab)$_2$. Also useful are any sub-fragments retaining the hypervariable, antigen-binding region of an immunoglobulin and having a size similar to or smaller than a Fab' fragment. This includes genetically-engineered or recombinant antibodies and proteins, whether single-chain or multiple-chain, which incorporate an antigen-binding site and otherwise function in vivo as targeting vehicles in substantially the same way as natural immunoglobulin fragments. (See, e.g., U.S. Pat. No. 4,946,778.) Fab' fragments may be conveniently made by reductive cleavage of F(ab')$_2$ fragments, which themselves may be made by pepsin digestion of intact immunoglobulin, under reducing conditions, or by cleavage of F(ab')$_2$ fragments which result from careful papain digestion of whole immunoglobulin. The fragments may also be produced by genetic engineering.

In certain preferred embodiments, the antibody or antibody fragment are humanized. In certain preferred embodiments, the humanized antibody can be anti-CEA, anti-TAG-72, antibodies.

Other useful antibodies include those having a specific immunoreactivity to a marker substance produced by or associated with the cancer cells of at least 60% and a cross-reactivity to other antigens or non-targeted substances of less than 35%. A monoclonal antibody that specifically targets tumor sites by binding to antigens produced by or associated with the tumors is particularly preferred. Antibodies against tumor antigens are known. For example, antibodies and antibody fragments that specifically bind markers produced by or associated with tumors have been disclosed. (See, e.g., U.S. Pat. Nos. 3,927,193, 4,331,647, 4,348,376, 4,361,544, 4,468,457, 4,444,744, 4,818,709 and 4,624,846.) In particular, antibodies against an antigen, e.g., a gastrointestinal, lung, breast, prostate, ovarian, testicular, brain or lymphatic tumor, a sarcoma or a melanoma, are advantageously used.

The antibodies and antigen-binding antibody fragments useful in the methods of the present invention may be linked to another group forming a conjugate by a variety of methods of chemical conjugation known in the art. (See, e.g., Childs, et al. 1985 *J. Nuc. Med.* 26:293.)

In certain embodiments, the targeting moiety is selected from the group consisting of proteins, small peptides, polypeptides, enzymes, hormones, steroids, cytokines, neurotransmitters, oligomers, vitamins and receptor binding molecules.

In certain embodiments, the first ligand group is selected from a Morpholino oligomer, an antibody fragment, or other specific groups.

Morpholino oligomers ("MORFs") are synthetic molecules that are the product of a redesign of natural nucleic acid structure, which could bind and inactivate selected RNA sequences. But for tumor pretargeting it is selected not binding to RNA. Structurally, the difference between MORFs and DNA is that while MORFs have standard nucleic acid bases, those bases are bound to morpholine rings instead of deoxyribose rings and linked through phosphorodiamidate groups instead of phosphates. (Summerton, et al. 1997 *Antisense & Nucleic Acid Drug Development* 7 (3): 187-95; U.S. Pat. Nos. 5,142,047 and 5,185,444.) MORFs are assembled from four monomers, each respectively has one of the four genetic bases (A, G, C, or T), linked to a six-membered morpholine ring.

In certain preferred embodiments, the first ligand group is a Morpholino oligomer (MORF) and the second ligand group is a biotin group. The MORF may comprise any suitable number of bases, for example, from about 6 bases to about 100 bases (e.g., from about 6 bases to about 50 bases, from about 6 bases to about 40 bases, from about 6 bases to about 30 bases, from about 10 bases to about 100 bases, from about 10 bases to about 50 bases). In certain preferred embodiments, the length of the MORF is from about 12 bases to about 30 bases. In certain preferred embodiments, the length of the MORF is from about 15 bases to about 25 bases (e.g., 15-mer, 18-mer, 20-mer). In certain preferred embodiments, the length of the MORF is from about 18 bases to about 25 bases. A complementary MORF is referred to as cMORF, for example, MORF15 and cMORF15 (15-mer), MORF18 and cMORF18 (18-mer) or MORF25 and cMORF25 (25-mer) are complimentary binding pairs.

In another aspect, the invention generally relates to a method for targeted delivery of an agent to a target site in a mammal. The method includes: (a) administering to the mammal a first compound. The first compound includes: a targeting moiety capable of selectively binding to a primary and specific target site or to a substance produced by or associated with the target site, a first conjugate comprising two covalently linked ligand groups, a first ligand group and a second ligand group, and a second conjugate formed by a covalently linkage between the targeting moiety and the first conjugate; (b) administering to the mammal a clearing agent comprising a group capable of selective binding to the second ligand; and (c) administering to the mammal an effector conjugate, wherein the effector conjugate comprises an agent covalently linked to a group capable of selective binding to the first ligand group.

The effector conjugate to be delivered to the target site may contain a therapeutic entity or a diagnostic probe. Exemplary therapeutic entities include antibodies, antibody fragments, drugs, toxins, nucleases, hormones, immunomodulators, chelators, boron compounds, photoactive agents or dyes and radioinuclides. Exemplary diagnostic probes include radionuclides, dyes, contrast agents, fluorescent compounds or molecules.

In certain preferred embodiments, the second ligand group is a biotin group along with a MORF as the first ligand group.

It is noted that any suitable clearing agents may be used in accordance with the present invention. For example, biotin or streptavidin may be used as the second ligand group in a clearing agent.

Any suitable routes of administration may be employed, for example, by intravenous, intraarterial, intrapleural, intraperitoneal, intrathecal, subcutaneous or perfusion administration.

The method of the invention may be utilized for detection or treatment of a variety of diseases and conditions, for example, tumors or other lesions, infectious diseases, inflammatory diseases and autoimmune diseases as well as human pancreatic islets in connection with diabetes.

In yet another aspect, the invention generally relates to a kit for delivering a diagnostic or therapeutic agent to a target site. The kit includes: (a) a compound that include: a targeting moiety capable of selectively binding to a primary and specific target site or to a substance produced by or associated with the target site, a first conjugate comprising two covalently linked ligand groups, a first ligand group and a second ligand group, and a covalent linkage between the targeting moiety and the first conjugate; (b) a clearing agent comprising a group capable of selective binding to the second ligand group; and (c) an effector conjugate, wherein the effector conjugate comprises an effecting group covalently linked to a group capable of selective binding to the first ligand group.

EXAMPLES

A MORF was designed that carries a group containing both biotin and a primary amine at 3'-end with its sequence the same as used previously reported (TCTTCTACTTCA-CAACTA). (Liu G, et al. 2004 *Eur J Nucl Med* 31: 417-24.). Hereafter in this manuscript, ($NH_2$-Biotin)-MORF is used for this amine-plus-biotin modified MORF to indicate both amine and biotin are attached to the MORF. The two functional entities in one group are put in a bracket and smaller group precedes the larger sequentially. Other similar structures will also be expressed following the same rule.

The TEZTM Biotin Quantitation Kit, streptavidin, and avidin were from Pierce (Thermo Fisher Scientific, Rockford, Ill.), while the streptavidin agarose sedimented bead suspension was from Life Technologies™ (Carlsbad, Calif.). The model antibody CC49 was prepared by Strategic Biosolutions (Ramona, Calif.) from the CC49 murine hybridoma cell line (a gift from Dr Jeff Schlom, Center for Cancer Research, NCI, NIH). Modification of the antibody with the ($NH_2$-Biotin)-MORF utilized a Hydralink kit consisting of paired agents of C6-SANH (a succinimidyl-activated hydrazinonicotinate acetone hydrazone) and C6-SFB (a succinimidylactivated formylbenzoate) from Solulink Biosciences (San Diego, Calif.). All other chemicals were reagent grade and used without purification.

The concentrations of MORF and cMORF were determined by UV spectrophotometry using the molar absorbance from the provider. Size exclusion (SE) HPLC was used for their analysis. The HPLC system was equipped with a superpose-12 10/30 GL column (from GE Healthcare Bio-Sciences AB, Uppsala, Sweden, optimal separation range: $1 \times 10^3$ to $3 \times 10^5$ Da) or a Superdex™ 75 column (optimal separation range: $1 \times 10^2$ to $7 \times 10^3$ Da; Amersham Pharmacia Biotech, Piscataway, N.J.), a UV in-line detector, and a radioactivity in-line detector. The eluant of 0.10 M pH 7.2 phosphate buffer was commonly used at a flow rate of 0.60 mL/min, unless the 10% ACN-0.10 M $NH_4Cl$ solution was required for streptavidin/biotin binding studies. Radioactivity recovery was routinely measured and was always greater than 90%.

Figure 3:
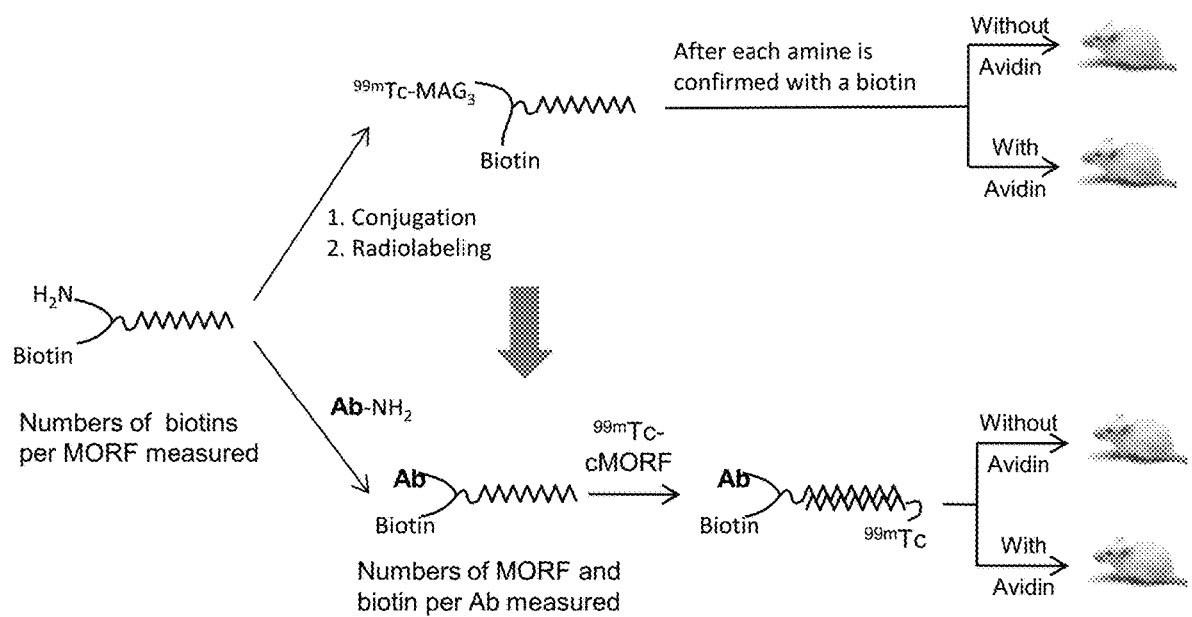
FIG. 3 shows a scheme for constructing a completely clearable (MORF-biotin)-Ab and evaluating the avidin clearance effect.

The experimental design for constructing and validating the antibody conjugate compound is as depicted in the flow chart of FIG. 3. First measured was the average number of biotin on the MORF and then, to confirm each amine was with a biotin, the amine on the MORF was radiolabeled. With this radiolabeled biotin-MORF, it was also determined whether avidin could clear the labeled ($NH_2$-biotin)-MORF into liver prior to conjugating it onto a model antibody (an antiTAG-72 antitumor antibody CC49). After synthesis of the (biotin-MORF)-CC49, the numbers of MORF and biotin per antibody were measured. Finally, it was evaluated the clearance efficiency of (biotin-MORF)-CC49 by avidin. Adding $^{99m}$Tc-cMORF to bind to the pendent MORF creates a label to the antibody.

In a second investigation, the clearance efficiency was investigated to differentiate the influences of each factor in a pretargeting protocol, including the non-biotinylated MORF-antibody, the long pretargeting time, and the accessibility of antibody to the avidin.

One study was designed to figure out why a small portion of (biotin-MORF)-CC49 (4%) was non-clearable. The linkage between the antibody and the ($NH_2$-biotin)-MORF was formed by the reaction of the $NH_2$ group to the NHS-ester linker. We suspect the unmodified impurity may react with the NHS ester to a very less extent although theoretically not do so. Thus, a NHS-$MAG_3$ that was able to be labeled after conjugation was used as a model NHS-ester to investigate the reaction of NHS-ester with the modified MORFs.

Number of Biotin on ($NH_2$-Biotin)-MORF

The number of biotin on ($NH_2$-biotin)-MORF (i.e., the efficiency of terminal modification or the percent of modified MORF in the product) was measured using EZTM Biotin Quantitation Kit on a spectrophotometer as described previously. (Liu, et al. 2010 *Cancer Biother Radiopharm.* 25:757-62.) In the kit, HABA was bound to avidin and in color, but replacement by biotin released and decolorized it such that the decrease in optical density was proportional to amount of biotin. The average biotins per MORF were the ratio of biotin over MORF concentrations.

The number of biotin was also measured by SE-HPLC after adding streptavidin in excess to the ($NH_2$-biotin)-MORF. The MORF without the ($NH_2$-biotin) modification would not bind to streptavidin and therefore should remain at the original position. Inclusion of an internal standard (o-iodohippuric acid) allowed for quantitating the remaining unbound (unshiftable) MORF. The number of biotin was calculated by (100%–the percent of unshiftable MORF).

Figure 4:
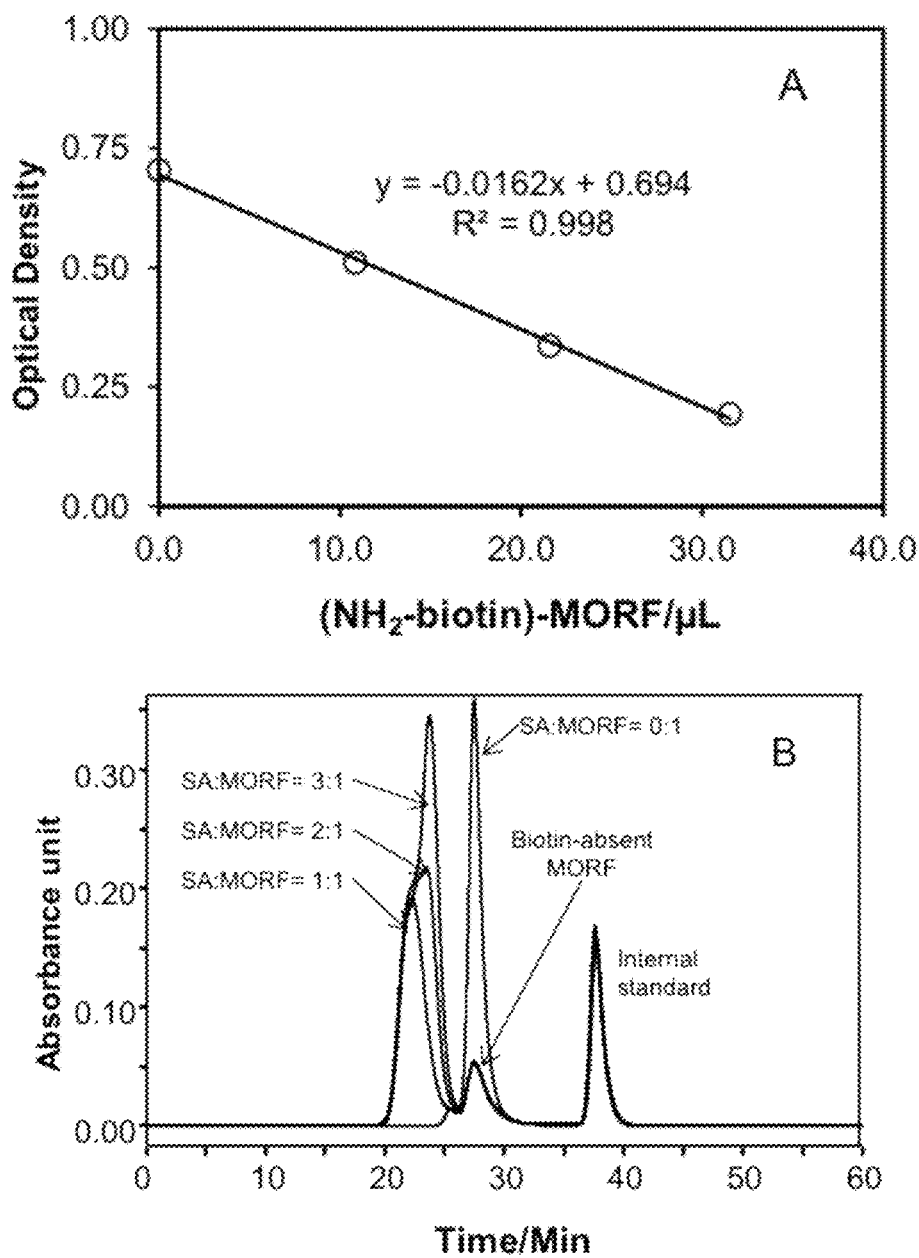
FIG. 4 shows (A) absorbance of the reaction mixture of 15 µL of HABA-avidin complex and increasing amount (0.889 µg/µL) of ($NH_2$-biotin)-MORF in a reaction buffer, and (B) HPLC traces at UV 265 nm of a mixture containing the ($NH_2$-biotin)-MORF, an internal standard of iodohippuric acid, and increasing amounts of streptavidin (SA).

The results measuring the biotins on the ($NH_2$-biotin)-MORF by the EZTM kit method and the HPLC "shifting" method were shown in FIGS. 4A and 4B. The OD in the Kit method decreases linearly with the amount of MORF added, yielding a value of 0.64 biotins per MORF and suggesting an incomplete modification. The incomplete modification was further confirmed by the HPLC method. As shown, addition of SA to ($NH_2$-biotin)-MORF at 1:1 results in a low MORF peak but more SA does not further reduce the peak, suggesting the remaining molecules lack a biotin group. The percentage bound to streptavidin, i.e., the number of biotin, was quantitated using the internal standard as $1-(\text{Peak area}_{MORF}/\text{Standard})_{SA:MORF=n:1}/$ (Peak area$_{MORF}$/$_{Standard}$)$_{SA:MORF=0:1}$, (n=1, 2, and 3). The average from the three samples=0.75±0.01 biotins per MORF.

Co-Existence of Amine with Biotin in (NH$_2$-Biotin)-MORF

Similarly to "the shifting" of the native (NH$_2$-biotin)-MORF on HPLC by an amount of streptavidin in excess, the coexistence of the amine with the biotin was determined shifting the $^{99m}$Tc radiolabeled (NH$_2$-biotin)-MORF at the amine position. The procedures for conjugating with MAG$_3$ and labeling with $^{99m}$Tc were identical to those described for the NH$_2$-cMORF previously. (Liu, et al. 2006 *Appl Radiat Isot.* 64:971-978.) The peak of ($^{99m}$Tc-biotin)-MORF should shift completely even in the presence of unmodified MORF if each amine (and therefore $^{99m}$Tc) on MORF was together with a biotin.

The coexistence was secondly confirmed by streptavidin-coated beads. After washing three small spin column filled with the beads twice with 2% bovine serum albumin in PBS buffer, the ($^{99m}$Tc-biotin)-MORF was loaded to each followed by washing twice again. The eluate collections contained the $^{99m}$Tc labeled MORF that was non-biotinylated similarly to the negative controls of avidin-bound ($^{99m}$Tc-biotin)-MORF and a biotin-free $^{99m}$Tc-MORF (made exactly following previous protocols. (Liu, et al. 2006 *Appl Radiat Isot.* 64:971-978.)

Figure 5:
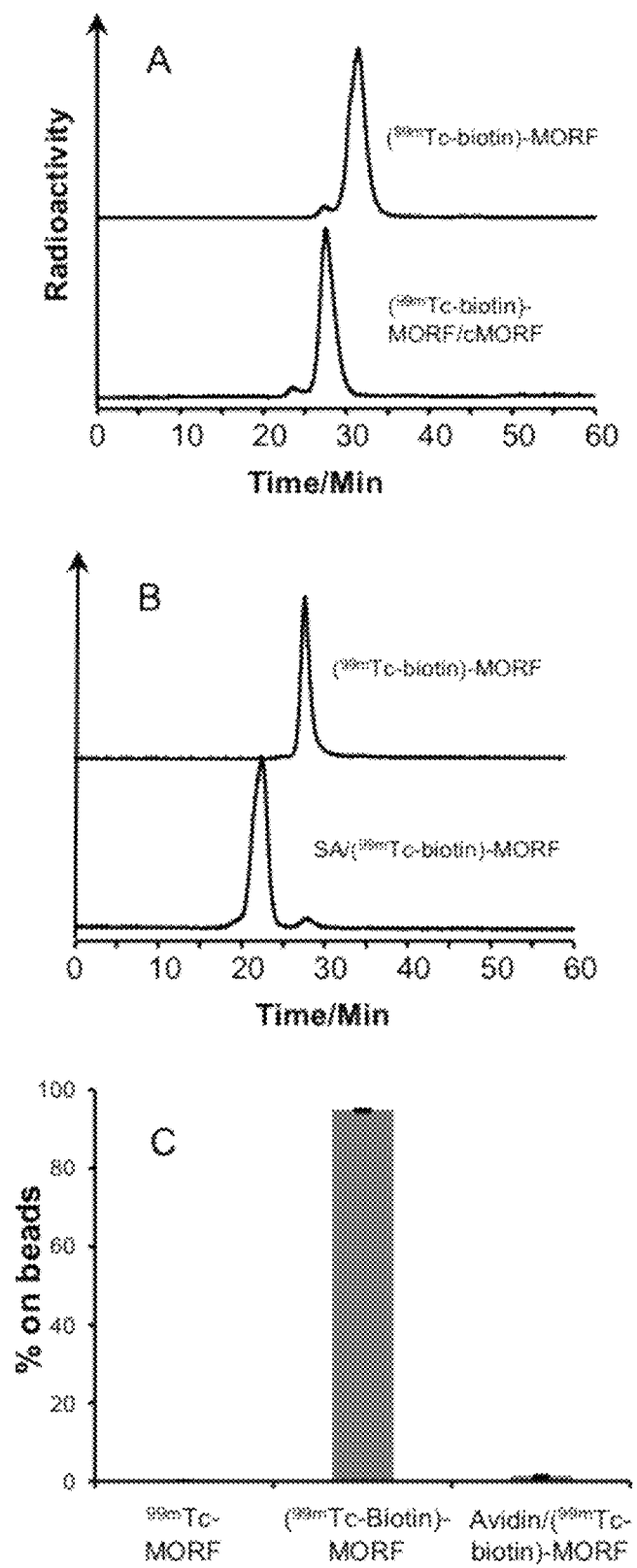
FIG. 5 shows HPLC traces of $^{99m}$Tc labeled ($NH_2$-biotin)-MORF (A) before and after adding excessive cold cMORF or (B) before and after adding excessive SA. (C) shows the radioactivity uptakes of $^{99m}$Tc labeled ($NH_2$-biotin)-MORF on streptavidin beads along with the negative controls of the biotin-free $^{99m}$Tc-MORF and the avidin-saturated ($^{99m}$Tc-biotin)-MORF.

Size-exclusion purification of MAG$_3$-conjugated (NH$_2$-biotin)-MORF, i.e., (MAG$_3$-biotin)-MORF, may contain non-modified MORF impurities. However, the radiolabeled (MAG$_3$-biotin)-MORF is shifted reasonably completely by the cMORF as shown in FIG. 5A. This indicated that the specific binding of the MORF is preserved instead of contradicting to the incomplete modification because the unmodified MORF does not carry a label to contribute. FIG. 5B further showed that all of the ($^{99m}$Tc-biotin)-MORF is almost completely shifted by SA (96%), suggesting that the amine site is with a biotin. FIG. 5C confirms this result by the fact that the ($^{99m}$Tc-biotin)-MORF will bind to the streptavidin beads unlike the biotin-free control $^{99m}$Tc-MORF or the avidin-blocked ($^{99m}$Tc-biotin)-MORF.

Conjugation of (NH$_2$-Biotin)-MORF to a Model Antibody

The conjugation of (NH$_2$-biotin)-MORF to an antibody using the commercial Hydralink approach was the same as that for the NH$_2$-MORF. (He, et al. 2007 *Bioconju Chem.* 18: 983-988; Liu, et al. 2010 *Q J Nucl Med Mol Imaging* 54:333-40.) Briefly, a model antibody of CC49 and the MORF were respectively conjugated with C6-SANH and C6-SFB followed by size-exclusion purification. Combination of the SANH-modified antibody and the SFB-modified MORF formed a hydrazone link between the antibody and MORF as shown below. A 1×50 cm Sephadex G-100 glass Econo-column was used for the purification of the MORF-antibody. The unmodified MORF impurity, if any, could be removed along with the unreacted (NH$_2$-biotin)-MORF. The average biotins and MORFs per antibody were determined as described previously. (Liu, et al. 2010 *Cancer Biother Radiopharm.* 25:757-62.)

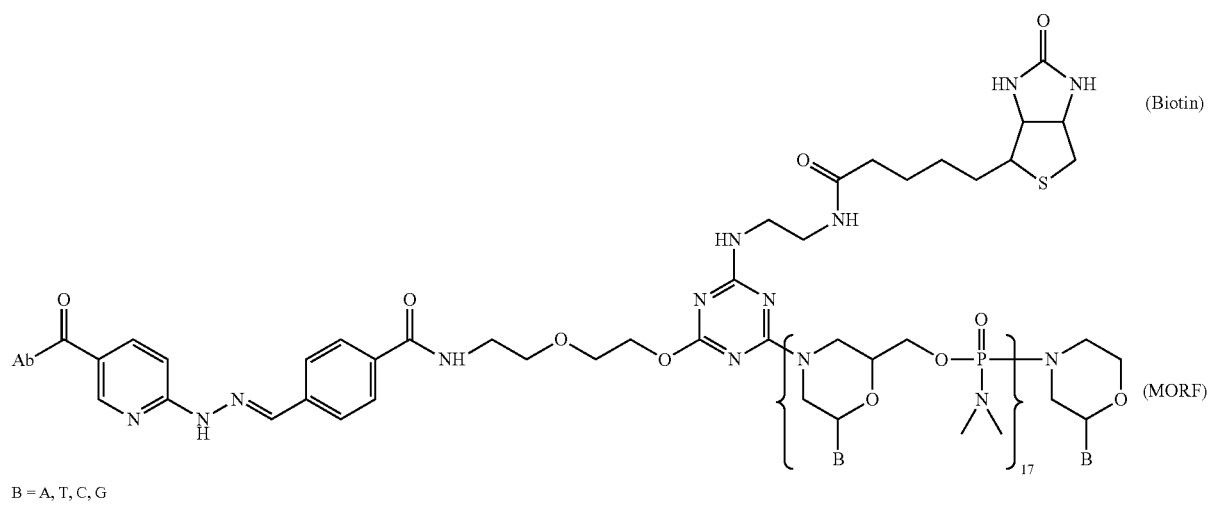

B = A, T, C, G

Clearance of (Biotin-MORF)-Antibody by Avidin

To avoid unnecessary efforts and to facilitate later interpretation of the antibody data, prior to synthesizing the (biotin-MORF)-antibody, the avidin-bound ($^{99m}$Tc-biotin)-MORF was administered to mice. After confirming the avidin clearance effect and subsequent success in conjugating (NH$_2$-biotin-MORF) to antibody, the antibody construct was labeled by adding tracer amount of $^{99m}$Tc-cMORF and evaluated for the avidin clearance. The $^{99m}$Tc-cMORF was obtained from instant labeling of a MAG$_3$-MORF stock solution. (Liu, et al. 2006 *Appl Radiat Isot.* 64:971-978.) The clearance studies by avidin included two injectates for in each case: an avidin-added for clearance and the other without avidin as a negative control. All animal use was in accordance with the guidelines of the Animal Care and Use Committee of the University of Massachusetts Medical School and conformed to the recommendations in the *Guide for the Care and Use of Laboratory Animals* (Institute of Laboratory Animal Resources, National Research Council, National Academy of Sciences, 1996).

In animals for testing the antibody construct, an injectate containing 30 µg of (biotin-CC49)-MORF/cMORF-$^{99m}$Tc (43 µCi, 1.17 MORF-biotins per CC49, MORF/cMORF ratio=2) or 30 µg of the antibody complex plus 80 µg of avidin (avidin/MORF or avidin/biotin=5) was administered to each of 20 CD-1 mice. They were divided into 5 groups (N=4) and euthanized at 2 min, 30 min, 1 h, 2 h, and 4 h. Organs were removed, weighed, and counted in an autogamma counter along with the injectate standards following our routine procedure and the % ID and % ID/g values were calculated. (Liu G, et al. 2004 *Eur J Nucl Med* 31: 417-24.)

For the ($^{99m}$Tc-biotin)-MORF, 1.0 µg (50 µCi) was administrated and the avidin/biotin ratio in the study injectate was also 5. Six groups of 4 mice were used and euthanized within a shorter period at 2 min, 12 min, 30 min, 1 h, 2 h, and 3 h, because the small MORF not attaching to an antibody cleared much faster.

Organs of especial interests for evaluating the clearance efficacy by avidin include blood, to observe how fast a biotinylated agent leaves the circulation; liver, to confirm whether avidin clears the biotinylated agents into this organ; whole body, to determine how much of the agent is completely out; and kidney, particularly relating to the labeled MORF oligomer, to check whether the clearance pathway has been altered.

Figure 6:
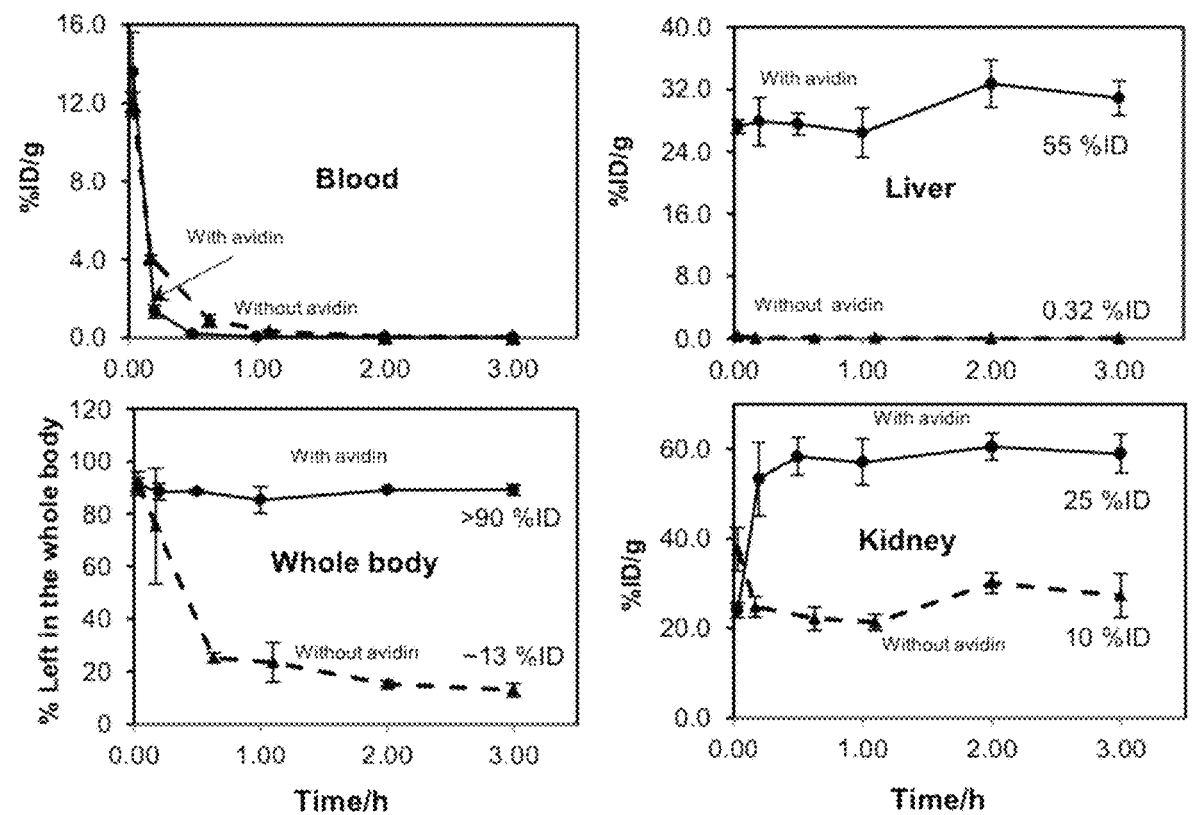
FIG. 6 shows radioactivity levels of avidin-bound (solid circle) and non-avidin-bound (solid triangle) (A) ($^{99m}$Tc-biotin)-MORF and (B) (biotin-CC49)-MORF/cMORF-$^{99m}$Tc in blood, liver, whole body, and kidneys over time.
Figure 6:
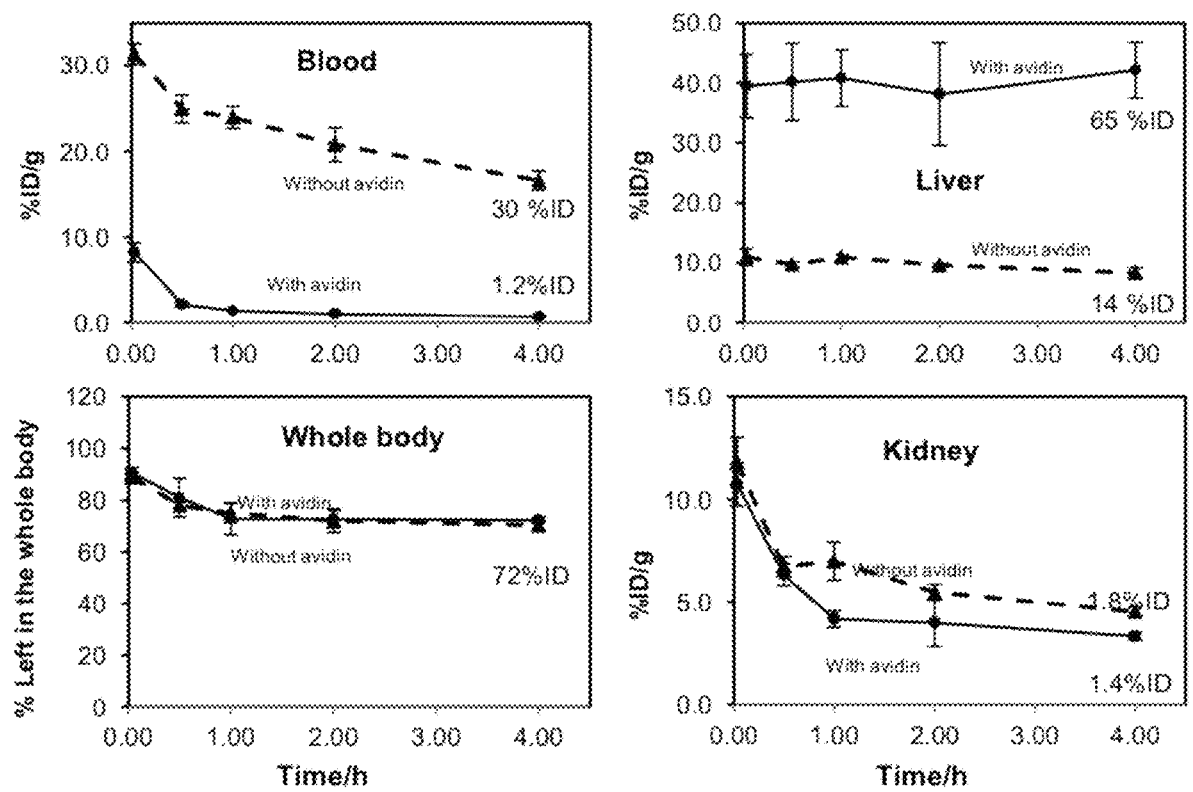

As shown in FIG. 6A, the ($^{99m}$Tc-biotin)-MORF clears rapidly from blood just like the previous biotin-free $^{99m}$Tc-MORF, but after binding to avidin, the blood clearance is further accelerated. The avidin effect can be appreciated more easily from the liver level difference, an accumulation of 55% ID with avidin at 3 h at 172-folds of that without avidin (0.32% ID). The free ($^{99m}$Tc-biotin)-MORF leaves the body through kidneys rapidly with only ~13% ID left in the body at 3 h (excluding bladder). Almost nowhere retains except kidneys (10% ID). When bound to avidin, the ($^{99m}$Tc-biotin)-MORF remains in the whole body although rapidly leaves the circulation. Its kidney accumulation is twice higher than that of the free ($^{99m}$Tc-biotin)-MORF but not excreting through this organ.

The (biotin-MORF)-antibody/cMORF-$^{99m}$Tc is much bigger in size compared to the ($^{99m}$Tc-biotin)-MORF (160 kDa vs 6 kDa), leading to a striking difference in clearance rate from blood or circulation as shown in FIGS. 6A and 6B. Therefore, the avidin effect becomes prominent even in the blood. The clearance efficiency at 4 h is at (30−1.2)/30*100%=96%, in coincidence with the 96% streptavidin-shiftable ($^{99m}$Tc-biotin)-MORF. Avidin clearance in blood takes about 1 h compared to the almost immediate for the ($^{99m}$Tc-biotin)-MORF. Also because of the bigger size, consistent to normal radiolabeled antibodies, it gets into liver by itself, but after bound to avidin, it clears to liver at a much higher rate and greater percentage as compared to the ($^{99m}$Tc-biotin)-MORF. (Cansow 1991 Nucl Med Biol 18: 369-381.) Again because of the bigger size, either bound to avidin or not, the labeled antibody construct does not excrete through kidneys and not even accumulate there (only 1.4-1.8% ID). Irrespective of the avidin-bound status, the whole body retention is identically high within the observation period, because the label on the antibody accumulated in liver either naturally or by avidin excretes slowly.

Clearance Efficiency by a Clearance Step with Varying Pretargeting Interval

Because a longer wait also reduces the non-specific background, pretargeting interval and avidin clearance as to their clearance effects were examined. The effect of avidin (clearance efficiency) is defined as the percentage of blood concentration reduction by avidin clearance as compared to the control without avidin clearance. The biotin-antibody-MORF was prepared from the old art with more than 12% is not clearable. This experiment was conducted to show the state of the MORF-antibody in blood. To completely label the antibody in vivo, the cMORF amount is in a molar excess of many folds as compared to the MORF on the antibody, such that the blood level of the cMORF is proportional to that of the antibody and can be used as a measure of the antibody blood level. The relationship is: % ID/$g_{antibody}$=% ID/$g_{cMORF}$/(Molar dose ratio of cMORF/antibody×MORF number per antibody). We note the actual antibody level is higher than the cMORF level because only a very small portion of the rapidly-clearing cMORF is consumed for binding to the MORF-antibody.

In a study set of 3 groups of mice (N=4), each of the 12 mice received via tail vein 30 µg of biotin-CC49-MORF (0.67 MORFs and 3.41 biotins per antibody); 1, 2, or 3 days later, an avidin dose of 34 µg was administrated intravenously to each of the 4 mice of the 3 groups followed 3 h later by the injection of 1.2 µg (80 µCi) of $^{99m}$Tc-cMORF. The mice were euthanized for biodistribution at 3 h subsequent to the radioactivity injection. In a control study, an otherwise identical procedure was applied except for the removal of the avidin injection. The 1.2 µg of cMORF was an optimized mass dose that was sufficient to saturate the MORF-antibody and the 34 µg of avidin was previously determined to be more than sufficient to saturate the biotin-modified MORF-antibodies in the circulation. (Liu, et al. 2010 Cancer Biother. Radiopharm. 25, 757-762.) The decrease of blood radioactivity level was proportional to the decease of the MORF-antibody level and was used as the measure of background improvement. The clearance efficiency (=100%−the ratio of the blood levels of radioactivity with or without avidin injection) was used to quantify the clearance effect of avidin.

Figure 7:
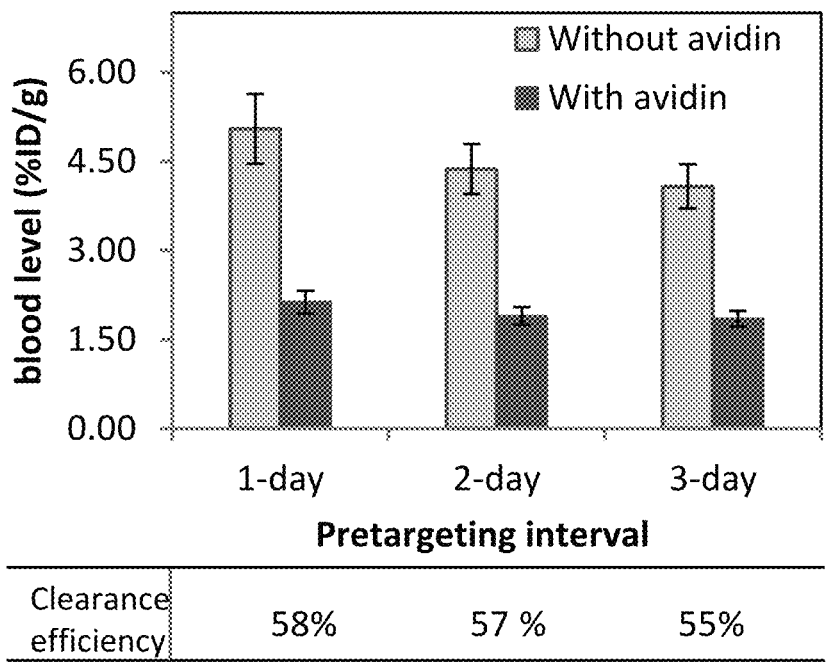
FIG. 7. Clearance efficiency for different pretargeting intervals in a pretargeting procedure using biotin-CC49-MORF, avidin, and $^{99m}$Tc-cMORF. The clearance efficiency is defined as (1−the ratio of blood level with/without avidin).

Both prolonging the pretargeting interval and the use of avidin reduced the antibody levels in blood (FIG. 7) and normal tissues (not presented), but the use of avidin is more effective. The clearance efficiency using avidin as a clearing agent is 55-58%, i.e., with >40% antibody remaining in the circulation. The MORF-antibody molecules cleared from circulation and the remaining seem equally clearable, because varying the pretargeting interval did not considerably change the clearance efficiency (FIG. 7).

Figure 8:
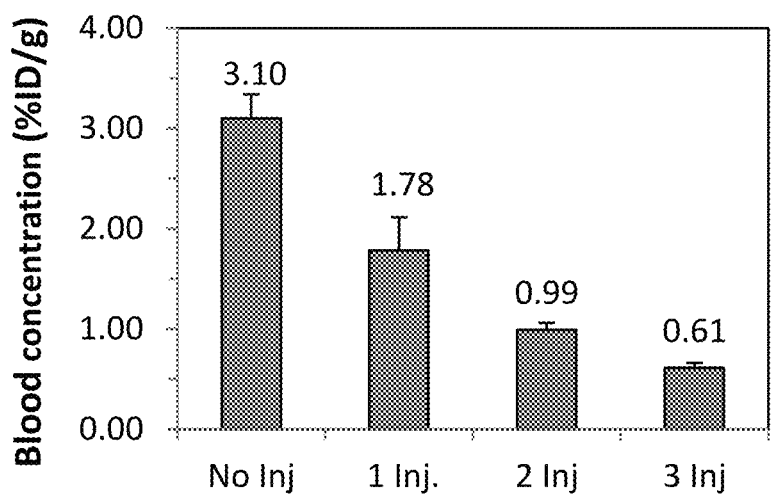
FIG. 8. The blood radioactivity levels after a procedure including injection of the biotin-Ab-MORF, different number of injections of avidin, and the injection of the raidolabeled cMORF. The time of euthanization of the mice was at 4 days after initial injection of the pretargeting antibody and 3 h after injection of radiolabeled cMORF (see Methods).

As confirmed in FIG. 8, the additional injections of 33.4 µg of avidin to the pretargeted animals subsequent to the first further reduce the blood concentration of antibody. This suggests that the majority of antibody molecules that survived the first avidin injection are clearable, consistent with the expectation from the 88% of the clearable avidin-treated antibody measured using the method disclosed herein above. The collective clearance efficiency following 3 avidin injections is 80% (0.61/3.10*100%). The separate clearance efficiency following each injection is 43% (1−1.78/3.10), 44% (1−0.99/1.78), and 38% (1−0.61/0.99) respectively. The real clearance efficiency may be actually higher because of the non-clearable portion. A calculation based on a constant clearance efficiency of 51%, and the non-clearable portion of 12% provides the blood concentrations of 3.10, 1.71, 1.03, 0.69% ID/g. These numbers are in a good agreement to the measured 3.10±0.24, 1.78±0.33, 0.99±0.07, 0.61±0.05% ID/g.

The in vivo interaction between antibody and clearing agent has become clear now. The results should be useful for both immunotherapy using antibody-drug conjugates as well as for immunoradiotherapy using pretargeting. We demonstrated the every avidin bound antibody molecule in blood leaves the circulation very rapidly, differentiated the temporarily non-clearable and the real non-clearable antibody, and turned the previous hypotheses into facts. The multiple injection study confirms the temporary on-clearable concept and supports that a continuous administration (infusion) of the clearing agents generates a complete clearance of the clearable MORF-antibody and is suitable for the future clinical applications.

Figure 9:
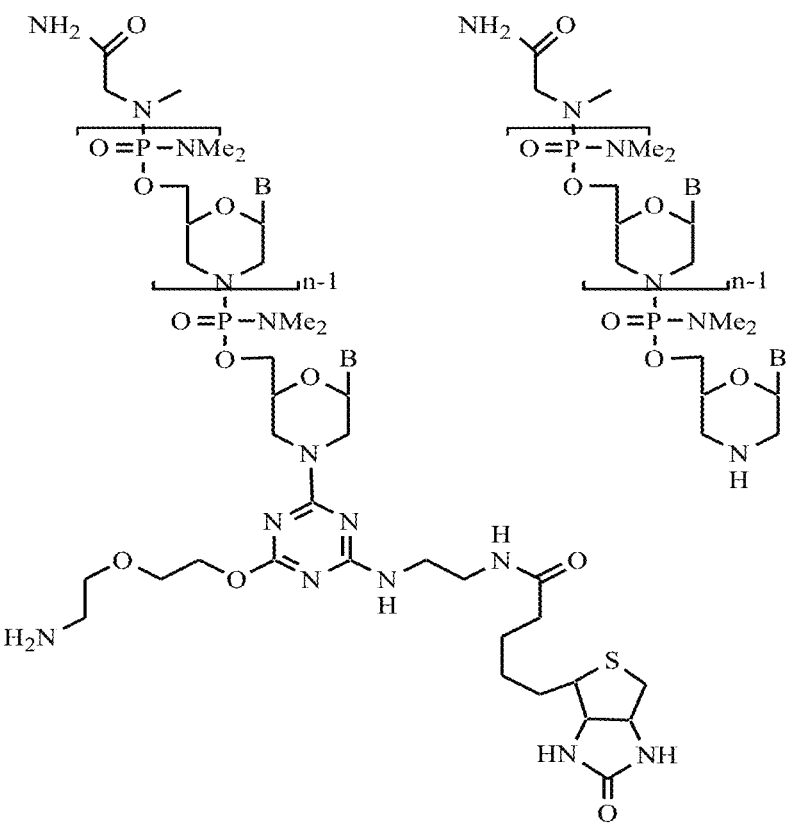
FIG. 9. The structures of ($NH_2$-biotin)-MORF and native MORF.

Reaction of NHS-Activated Ester with Primary Amine-Derivatized DNA Analogue and Non-Derivatized Impurity This experiment was designed to figure out why the 4% of (biotin-MORF)-CC49 was non-clearable. The linkage between the antibody and the ($NH_2$-biotin)-MORF was formed by the reaction of the $NH_2$ group to the NHS-ester linker. We suspect the unmodified impurity may react with the NHS ester to a very less extent although theoretically not do so. Thus, a NHS-$MAG_3$ that was able to be labeled after conjugation was used as a model NHS-ester to investigate the reaction of NHS-ester with the modified MORFs. As shown in FIG. 9, the amine in the modified MORF is a primary amine and terminal of the un-modified amine is a secondary amine. We conjugated a mixture of an amine-derivatized MORF and a native MORF with NHS-$MAG_3$ and radiolabeled the conjugates for investigation. In the primary amine-derivatized MORF, the biotin concomitantly with the primary amine was used for streptavidin (SA)-mediated discrimination between the conjugate of ($NH_2$-Biotin)-MORF and that of non-derivatized (or native) MORF. If the labeled MORF did not bind to SA, then the $MAG_3$-MORF was formed by side reactions instead of by reacting to the primary amine.

The MORF and its complement (cMORF) were custom-synthesized by Gene-Tools (Philomath, Oreg.). The MORF was also derivatized by attaching a primary amine-plus-biotin group to the 3'-equivalent terminus by the company. The MORF sequence was (5'-TCTTCTACTTCACAACTA) and the terminal structures of the two MORFs are illustrated in FIG. 9. The S-acetyl NHS-$MAG_3$ was previously synthesized in house. (Liu, et al. 2002 *Bioconjug. Chem.* 13: 893-897.) The EZ™ Biotin Quantitation Kit and the streptavidin were from Pierce (Thermo Fisher Scientific, Rockford, Ill.). The P-4 resin (Bio-Gel P-4 Gel, medium) was from Bio-Rad Laboratories (Hercules, Calif.). The $^{99}$Mo-$^{99m}$Tc generator was from Perkin Elmer Life Science Inc (Boston, Mass.). All other chemicals were reagent grade and were used without purification.

Figure 10:
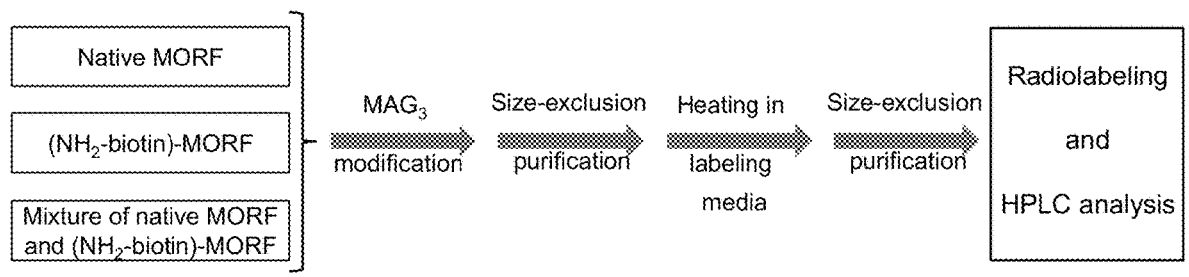
FIG. 10. A scheme describing the $MAG_3$ conjugation to the MORFs and purification for $^{99m}$Tc labeling.

As shown in FIG. 10, the ($NH_2$-biotin)-MORF, the native MORF control, and a 50/50 mixture of the two were treated with the S-acetyl NHS-$MAG_3$ following a reported protocol. (Liu, et al. 2006 *Appl. Radiat. Isot.* 64: 971-978.) 1.5 mg of MORF was dissolved in 0.2 M, pH 8.0 HEPES to a concentration of 0.5 mg/mL. The solution was added to a vial containing S-acetyl NHS-$MAG_3$ such that the $MAG_3$/MORF molar ratio was 20. After 2 h incubation at room temperature, the reaction mixture was purified over a P4 column (0.7×20 cm) using 0.25 M $NH_4$OAc at pH 5.2 as eluent. The peak fractions with optical density (OD) value at 265 nm greater than 5 were pooled. Subsequently, a procedure was performed to dissociate the unstable $MAG_3$-MORF conjugate. The MORF solution was mixed with a tartrate buffer (pH 9.2, 50 μg/μL $Na_2$ Tartrate.$2H_2O$ in a solution of 0.5 M $Na_2HCO_3$, 0.25 M $NH_4$OAc, and 0.175 M $NH_3$) and a fresh tin solution (10 μg/μL $SnCl_2$.$2H_2O$ and 1 μg/μL NaAscorbate in 10 mM HCl). The volume ratios of MORF solution/tartrate buffer/tin solution were 15/5/1. The mixed solution was heated at 100° C. for 20 min and purified again over a longer P4 column (1.0×50 cm), followed by pooling the peak fractions with OD values over 5 as the final stock conjugate solution.

Each $MAG_3$-conjugated MORF solution was labeled with $^{99m}$Tc. Between 5 and 50 μL of $^{99m}$Tc-pertechnetate generator eluate was added to a mixed solution of 30 μL of $MAG_3$-MORF solution (0.2-0.4 mg/mL MORF) in pH 5.2 $NH_4$OAc buffer, 10 μL of tartrate buffer, and 3 μL of 4 μg/μL $SnCl_2$.$2H_2O$ in ascorbate-HCl solution (1 μg/μL NaAscorbate in 10 mM HCl), followed by heating at 100° C. for 20 min.

To confirm that the radioactivity peak did represent faithfully the labeled MORFs, they were hybridized with cMORF. When the duplex formed, the labeled single-strand radioactivity peak shifted to the position of the duplex of doubled molecular weight. The cMORF was in a great excess (at a cMORF/MORF molar ratio of ~55) as compared to the labeled MORF. Thus, the cMORF were more than sufficient to bind any of the MORF preserving the hybridizing affinity.

The labeled MORFs were also reacted with SA such that any labeled MORF molecule that carried a biotin was shifted to the SA position or slightly further to the left. An excessive dose resulting in a molar ratio of SA/MORF=10:1 was used to assure a complete shift of the biotinylated MORF.

Figure 11:
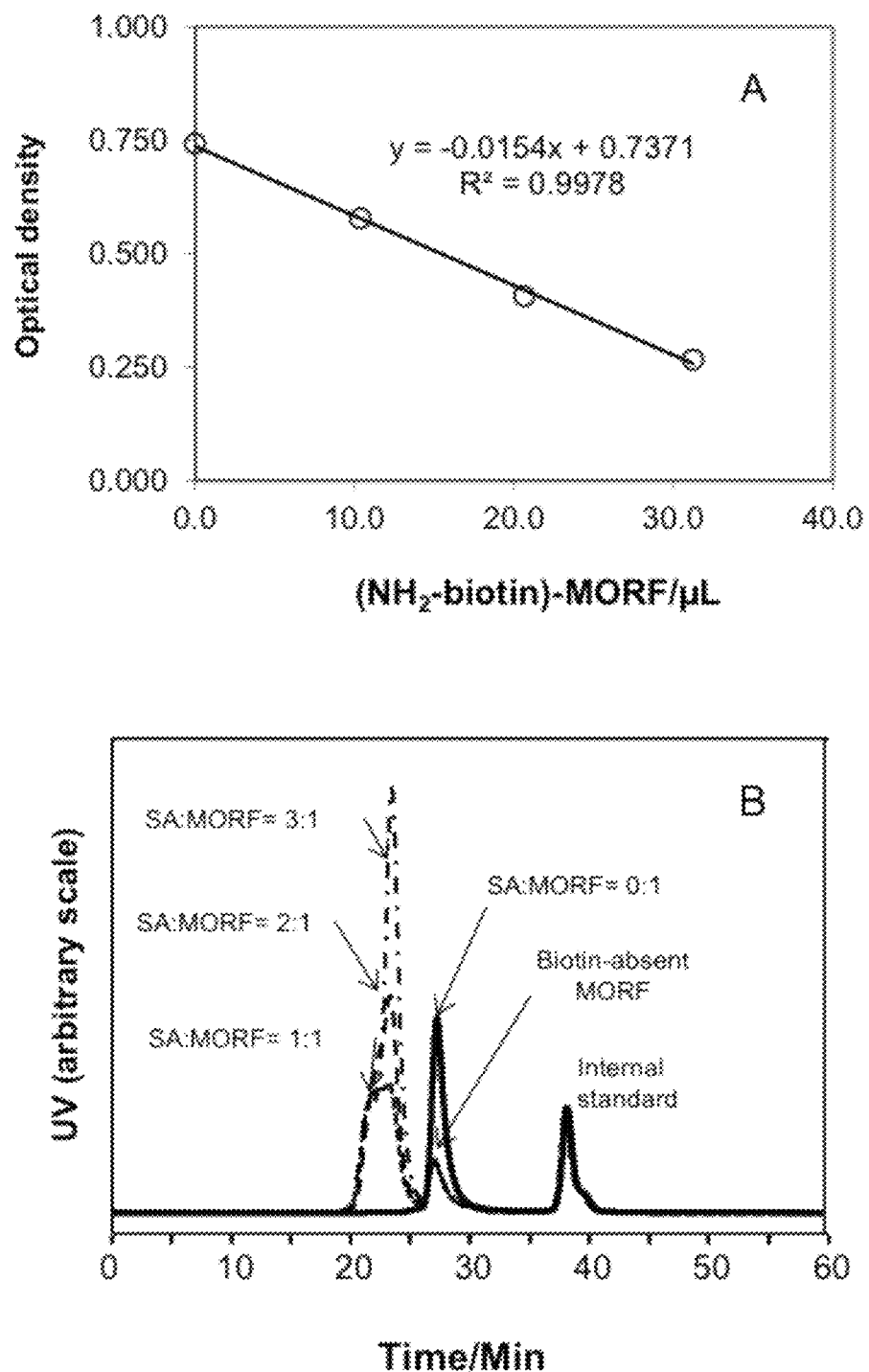
FIG. 11. (A) The OD values of the reaction mixture of 15 µL of HABA-avidin with an increasing amount of ($NH_2$-biotin)-MORF (0.798 µg/µL). (B) The HPLC traces at UV 265 nm of the ($NH_2$-biotin)-MORF mixed with an internal standard of iodohippuric acid after adding an increasing amount of streptavidin (SA).

The results from the detection by the EZ™ kit and from the HPLC "shifting" are shown in FIGS. 11A and 11B. The OD value from the kit method decreases linearly with increasing MORF added. The number of biotins per MORF is calculated to be 0.68 by the formula of (slope*MW*volume)/(34000*MORF concentration), a value of lower than 1 indicating an incomplete terminal derivatization. This result is consistent with the results from the HPLC method as shown in FIG. 11B. Addition of streptavidin to ($NH_2$-biotin)-MORF at a molar ratio of 1:1 "shifts" most of the MORF peak to the left. Further addition of streptavidin has no effect, confirming the residual MORF lacks the ($NH_2$-biotin). The fraction of residual peak area after addition of streptavidin was calculated to be 0.65±0.01 based on the formula of [1−residual peak $area_{n:1}$]/[original peak $area_{0:1}$], (n=1, 2 and 3).

Figure 12:
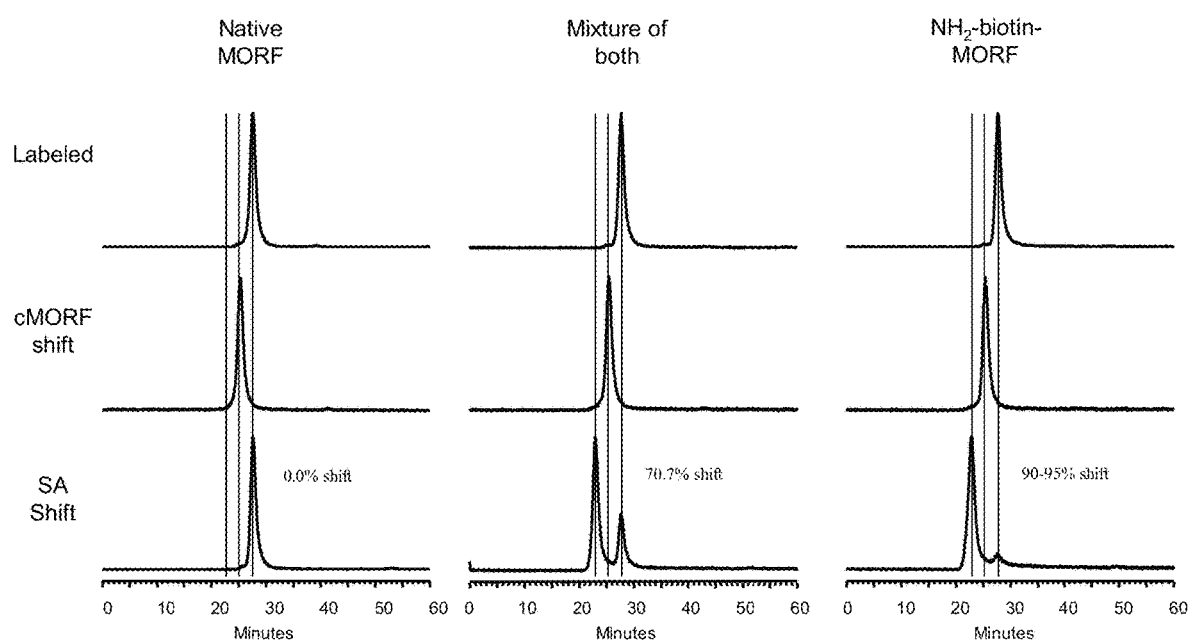
FIG. 12. The HPLC traces of native MORF, ($NH_2$-biotin)-MORF, and their 1:1 mixture after NHS-$MAG_3$ conjugation and radiolabeling (top row). Also shown are the peaks after addition of excess cMORF at a molar ratio of cMORF/MORF=55 (second row) and excess SA at a molar ratio of SA/MORF=10 (bottom row).

As shown in the top row of FIG. 12, after $MAG_3$ modification, both the ($NH_2$-biotin)-MORF and the native MORF can be labeled with high efficiency (>95%), confirming our suspicion. All can hybridize with the cMORF ($2^{nd}$ row), indicating the overall integrity of the sequence. The fact that the native MORF can be labeled indicates the NHS-ester also reacts with other groups in addition to the primary amine.

Nevertheless, the SA shifting indicates the ($NH_2$-biotin)-derivatized MORF reacts with the NHS ester in a much higher yield than the non-derivatized MORF. Certainly, the $^{99m}$Tc-$MAG_3$ labeled native MORF cannot be shifted by SA due to the lack of biotin. Most of the $^{99m}$Tc-$MAG_3$ labeled ($NH_2$-biotin)-MORF is shifted (~95%), reproducing our earlier results with another ($NH_2$-biotin)-MORF sample. The reactivity of the non-derivatized MORF with NHS-$MAG_3$ relative to that of the ($NH_2$-biotin)-derivatized MORF can be estimated theoretically, but the ~5% unshiftable residual is too small for an accurate estimation, which was the 1:1 mixture of ($NH_2$-biotin)-MORF and native MORF was included. Assuming the 35% of the ($NH_2$-biotin)-MORF sample is in the native form of the MORF (based on the absence of biotin and the personal communication with Dr Yongfu Li from Gene-Tools), the 70.7% shift for labeled mixture (middle of the bottom row) indicates that 5 molecules of ($NH_2$-biotin)-MORF reacted with the NHS ester for each of the native MORF molecules that reacted with the NHS ester. In other words, the reactivity of native MORF is 5 times weaker than the ($NH_2$-biotin)-MORF under the conditions of this investigation.

Figure 13:
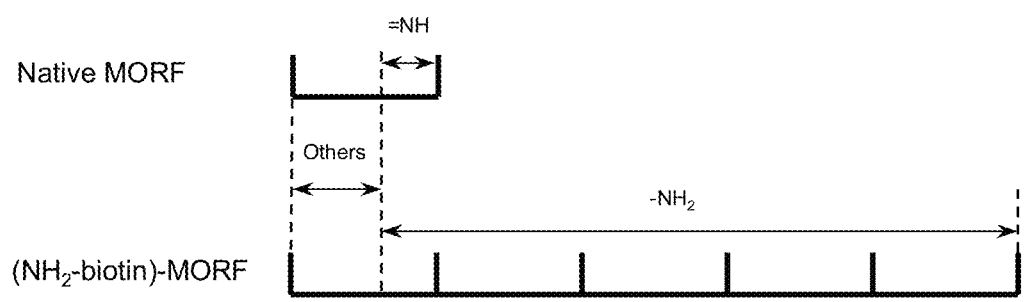
FIG. 13. The relative reactivity of ($NH_2$-biotin)-MORF to that of native-MORF.

Referring to FIG. 9, the reaction sites on the native MORF for the NHS-ester possibly include the 3'-primary amine and the aromatic amines in the residual bases. Those in the ($NH_2$-biotin)-MORF are the same except the 3'-terminal secondary amine is converted to a primary amine. The primary amine is much more active site than the secondary amine. As depicted in FIG. 13, the $MAG_3$ conjugation to the native MORF can be attributed to the secondary amine and others, although we do not know their exact relative contributions. For the (NH$_2$-biotin)-MORF, we similarly do not know the contribution of the other eaction sites than the terminal amine. Nevertheless, as seen in FIG. 13, we do know the 4-fold increase in reactivity is due to the primary amine, because the reactivity difference between native MORF and (NH$_2$-biotin)-MORF comes from the conversion of the secondary amine to the primary amine. In addition, the contribution from the secondary amine for the native MORF should now be credited to the primary amine, because the other possible reaction sites are identical. Thus, although the native MORF can be conjugated and provides an equally high labeling efficiency, the primary amine attached to the (NH$_2$-biotin)-MORF accounts for at least 80% of the entire MAG$_3$ conjugation. In reality, it may be closer to 90 or 95% as the secondary amine is more reactive than aromatic amines.

The above results apparently contradict with our previous assumption that the impurity of MORF would not interfere with the clearability of biotin-Antibody-MORF sample. Nevertheless, in addition to that the 4% biotin-Antibody-MORF sample can be now explained, it provides chemical evidence that the previous assumption is essentially reliable. Furthermore, if the (NH$_2$-biotin)-MORF is pure, our design will give rise to a completely clearable antibody conjugate.

In this specification and the appended claims, the singular forms "a," "an," and "the" include plural reference, unless the context clearly dictates otherwise.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A kit for delivering a diagnostic or therapeutic agent to a target site, the kit comprising:
a compound:

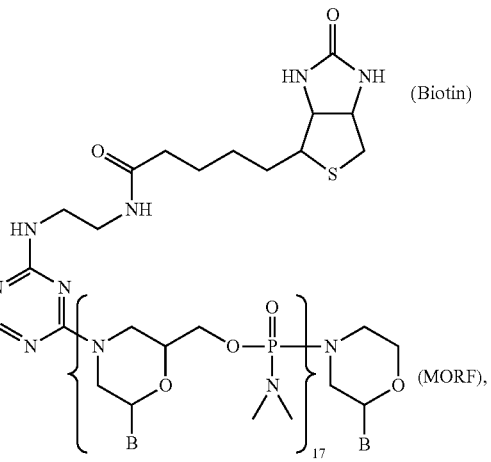

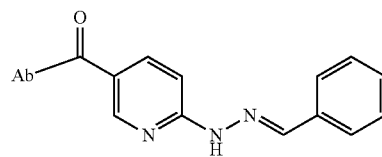

B = A, T, C, G

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

wherein Ab is an antibody or an antibody fragment;
a clearing agent comprising avidin; and
an effector conjugate comprising cMORF.

2. The kit of claim 1, wherein the antibody or antibody fragment is a tumor specific antibody or a tumor specific antibody fragment.

3. The kit of claim 2, wherein the antibody or antibody fragment are humanized.

* * * * *